United States Patent [19]

Sawayanagi et al.

[11] Patent Number: 5,387,518
[45] Date of Patent: Feb. 7, 1995

[54] ALKALINE PROTEASE HAVING STABILITY IN SOLUTION WITH ANIONIC SURFACTANT, METHOD FOR PRODUCING THE SAME, USE THEREOF AND MICROORGANISM PRODUCING THE SAME

[75] Inventors: Toyoji Sawayanagi; Mina Saito; Toshi Tsuzuki; Yoshio Fujiwara; Yoshitaka Noguchi, all of Tokyo, Japan

[73] Assignee: Showa Denko K.K., Tokyo, Japan

[21] Appl. No.: 873,168

[22] Filed: Apr. 24, 1992

[30] Foreign Application Priority Data

Apr. 26, 1991 [JP] Japan ................. 3-125457

[51] Int. Cl.$^6$ ............ C12N 9/50; C12N 9/52; C12N 9/54; C11D 17/00
[52] U.S. Cl. .................. 435/221; 435/219; 435/220; 252/174.12
[58] Field of Search .............. 435/219, 220, 221; 252/174.12

[56] References Cited

U.S. PATENT DOCUMENTS

| Re. 30,602 | 5/1981 | te Nijenhuis | 435/221 |
|---|---|---|---|
| 3,723,250 | 3/1973 | Aunstrup et al. | 435/221 |
| 3,827,938 | 8/1974 | Aunstrup et al. | 435/221 |
| 3,840,433 | 10/1974 | Aunstrup et al. | 435/221 |
| 3,871,963 | 5/1975 | Tobe et al. | 435/221 |
| 4,002,572 | 1/1977 | te Nijenhuis | 435/221 |
| 4,052,262 | 10/1977 | Horikoshi et al. | 435/221 |
| 4,480,037 | 10/1984 | Ichishima et al. | 435/221 |
| 4,581,332 | 4/1986 | Soejima et al. | 435/220 |
| 4,771,003 | 9/1988 | Stellwag et al. | 435/221 |
| 4,797,362 | 1/1989 | Takeuchi et al. | 435/221 |

FOREIGN PATENT DOCUMENTS 0495401 7/1992 European Pat. Off. ............ 435/221

OTHER PUBLICATIONS

Derwent Publications Ltd., London, GB; AN 91-290756 (40), (Aug. 21, 1991).
Derwent Publications Ltd., London, GB; JP-A-3 191 781, (Showa Denko), Aug. 21, 1991.

Primary Examiner—Douglas W. Robinson
Assistant Examiner—Jon P. Weber
Attorney, Agent, or Firm—Sughrue, Mion, Zinn, Macpeak & Seas

[57] ABSTRACT

An alkaline protease, method for producing the same and detergents containing the protease as an aid are disclosed. The alkaline protease is obtained by cultivating in a medium the microorganism SD523 FERM BP-3774 or artificial mutants or genetically engineered variants thereof which have the ability of producing the alkaline protease. The alkaline protease has: (1) an optimum pH of from about 11 to 11.5 as measured after reaction at 30° C. for 10 minutes using casein as a substrate and an optimum temperature of about 60° C. as measured after reaction at pH 10 using casein as a substrate; (2) a half inactivation temperature of about 55° C. as measured after reaction at pH 10 for 10 minutes; and (3) a molecular weight of 29,000±2,000 as measured by SDS polyacrylamide gel electrophoresis. The enzyme has improved storage ability in liquid detergents as compared with known alkaline proteases produced by known microorganisms belonging to the genus *Bacillus firmus*.

3 Claims, 6 Drawing Sheets

ALKALINE PROTEASE HAVING STABILITY IN SOLUTION WITH ANIONIC SURFACTANT, METHOD FOR PRODUCING THE SAME, USE THEREOF AND MICROORGANISM PRODUCING THE SAME

BACKGROUND OF THE INVENTION

1. Field of the Invention

The present invention relates to a novel alkaline protease, method for producing the same, use thereof, and a microorganism producing the protease.

2. Description of Prior Art

In accordance with recent trend that environmental pollution has been at stake and the use of phosphoric acid salts has been restricted increasingly, it has been proposed to compound enzymes with detergents to increase their washing power. Now, various detergents containing enzymes such as proteases, amylases, cellulases, and lipases, are commercially available.

Among the enzymes, proteases are deemed as an essential component of detergents because they decompose efficiently proteinaceous dirt which occupies 10 to 40% of organic dirt sticking to cloths and is difficult to be completely removed with non-enzymatic components of detergent only.

For the protease for detergents, many enzymes derived from microorganisms have hitherto been known.

While such enzymes have enough stabilities for use as an enzyme to be compounded in solid detergents, they have rather insufficient stabilities and are inactivated in a short time in the presence of detergent components at high concentrations in liquid detergents.

Accordingly, a number of technique have been proposed in order to increase the stability of the enzymes in liquid detergents, for example, by (1) development of novel surfactants, (2) addition of stabilizers, (3) microencapsulation of enzymes (cf. Japanese Patent Application Laid-Open No. 41398/1990 (=EP 352244), U.S. Pat. No. 4,287,082, British Patent No. 2,021,142, and Japanese Patent Application Laid-Open No. 596/1987 (=EP 199405) and No. 137996/1988).

However, there is a keen desire not only for a technique for stabilizing the enzymes but also for a novel enzyme itself that has an improved stability in liquid detergents.

SUMMARY OF THE INVENTION

Accordingly, an object of the present invention is to provide an alkaline protease having an excellent stability in the presence of the components of a liquid detergent, and also a microorganism producing such an enzyme.

Another object of the present invention is to provide an alkaline protease having an excellent stability in a detergent solution containing a surfactant at a relatively low concentration upon washing, and also a microorganism producing such an enzyme.

Still another object of the present invention is to provide an alkaline protease which can be supplied efficiently and at low cost, and also a microorganism producing such an enzyme.

In order to achieve the aforementioned objects of the present invention, the present inventors have carried out investigations and experiments in various detergent systems containing various surfactants and screened bacteria which can grow in the copresence of detergents. As a result, the present inventors have found that an enzyme produced by a species belonging to the genus Bacillus isolated from the soil in suburbs of Tokyo satisfies the aforementioned conditions. The present invention is based on this discovery.

As will be described in detail hereinbelow, the microorganism producing the enzyme of the present invention is judged to be a strain which belongs to the genus Bacillus, more specifically Bacillus firmus. Since it shows atypical behavior with respect to growing temperature and clearly differs from other known strains, the microorganism of the present invention has been acknowledged to be a new strain. The microorganism has been named "Bacillus SD523" by the present inventors.

That is, according to a first aspect of the present invention, there is provided an alkaline protease having the following properties:

(1) an activity for hydrolyzing proteins;
(2) an optimum pH of from about 11 to 11.5 as measured after reaction at 30° C. for 10 minutes using casein as a substrate;
(3) an optimum temperature of about 60° C. as measured after reaction at pH 10 using casein as a substrate;
(4) a heat resistance in terms of a half inactivation temperature of about from 55° to 57° C. as measured after incubation at pH 10 for 10 minutes; and
(5) a molecular weight of 29,000±2,000 as measured by electrophoresis using SDS polyacrylamide.

According to a second aspect of the present invention, there is provided a method for producing an alkaline protease, comprising the steps of: cultivating in a medium a microorganism SD523 FERM BP-3774 belonging to the genus Bacillus and having an ability of producing the above-described alkaline protease, artificial mutants or genetic engineered variants thereof; and collecting the objective alkaline protease from the medium.

According to a third aspect of the present invention, there is provided a microorganism SD523 FERM BP-3774 belonging to Bacillus firmus and having an ability of producing the above-described alkaline protease.

According to a fourth aspect of the present invention, there is provided an aid for detergents, comprising the above-described alkaline protease as an effective ingredient.

DETAILED DESCRIPTION OF THE INVENTION

Figure 1:
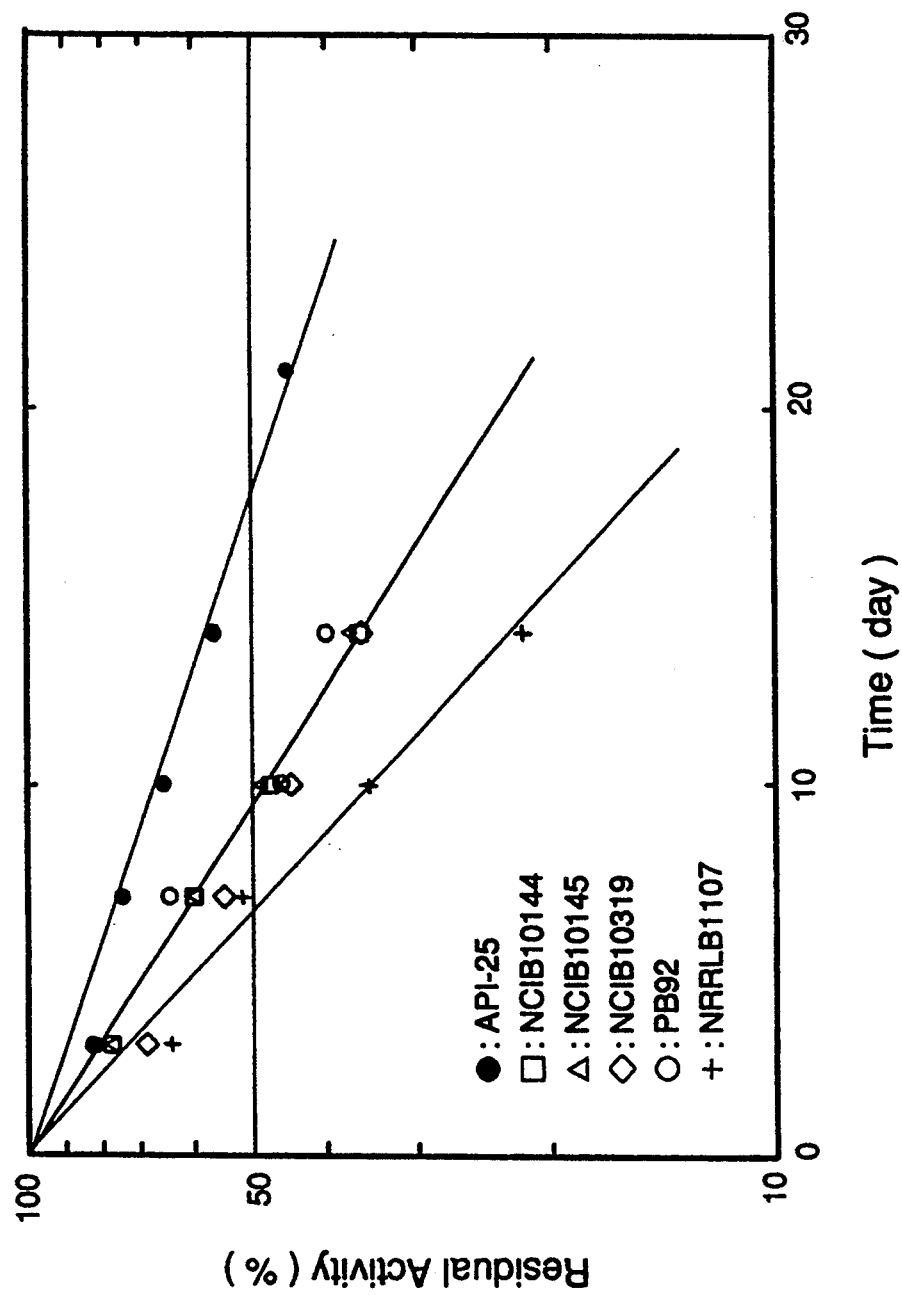
FIG. 1 is a graph illustrating storage stabilities of the enzyme of the present invention and conventional enzymes (5 types), respectively, in a model liquid detergent M-3.

Hereafter, detailed explanation will be made on the novel strain producing the alkaline protease of the present invention, the alkaline protease, method for producing it and its utility.

Alkaline Protease-Producing Microorganism

The novel strain SD523 used for producing the novel alkaline protease of the present invention is a bacterium belonging to the genus Bacillus, more specifically *Bacillus firmus*, and having an ability of producing alkaline protease having the aforementioned properties. The bacterium has the following bacteriological properties.

(A) Morphology
(a) Form and size of cell: Rod with a size of 0.4 to 0.6×1.0 to 3.0 μm.
(b) Polymorphism of cell: None.
(c) Motility: Flagellar movement.
(d) Spore formation: Forms elliptical spores with a size of 0.3 to 0.4 μm×0.4 to 0.5 μm, sporangium being slightly swollen, central to terminal.
(e) Gram stain: Positive.
(f) Acid-fast stain: Negative.

(B) Growth on the Following Media
(a) Meat broth agar plate medium: Grows at pH 7 forming circular, flat colonies with undulate periphery. Dull, cream-colored surface.
(b) Meat broth agar slant medium: Cloth spreading form at DH 7, forming cream-colored opaque colonies. No pigment.
(c) Meat broth liquid medium: Grows well with forming precipitates at pH 7. No pellicle formation.
(d) Meat broth gelatin stab culture medium: Liquefies gelatin at pH 7.
(e) Litmus milk: Liquefaction of milk is observed at pH 7. pH upon completion of cultivation is neutral.

(C) Physiological Properties
(a) Reduction of nitrates: Positive.
(b) Denitrification reaction: Negative.
(c) MR test: Negative.
(d) VP test: Negative (VP broth at pH 6.3).
(e) Production of hydrogen sulfide: Negative.
(f) Hydrolysis of starch: Positive.
(g) Assimilation of citric acid: Negative in Koser and Christensen media, respectively.
(h) Yolk reaction: Negative.
(i) Assimilation of inorganic nitrogen: Assimilates sodium nitrate and ammonium sulfate.
(j) Production of pigments: Negative.
(k) Urease: Negative.
(l) Oxidase: Positive.
(m) Catalase: Positive.
(n) Growth temperature range: Grows at 10° to 50° C. and grows well at 20° to 40° C.
(o) Growth pH range: Grows well at pH 7 to 10, but does not grow at pH 5.9 or less or at pH 11.2 or more.
(p) Behavior to oxygen: Aerobic. Impossible to grow under anaerobic conditions.
(q) O-F test: Oxidation.
(r) Resistance to sodium chloride: Grows in the presence of 7 % NaCl.
(s) Production of acid and gas from sugars: Tests were performed by setting up the initial pH of the medium to 8.6 at which good growth occurs. Results obtained are shown in Table 1 below.

TABLE 1

| Sugar | Acid | Gas |
|---|---|---|
| L-Arabinose | + | − |
| D-Xylose | − | − |
| D-Glucose | + | − |
| D-Mannose | + | − |
| D-Fructose | + | − |
| D-Galactose | − | − |
| Maltose | + | − |
| Sucrose | + | − |
| Lactose | − | − |
| Trehalose | + | − |
| D-Sorbitol | + | − |
| D-Mannitol | + | − |
| Inositol | − | − |
| Glycerol | + | − |
| Starch | + | − |
| Cellobiose | + | − |
| Raffinose | − | − |
| Ribose | + | − |

Notes: "+" indicates production, and "−" no production.

The aforementioned bacteriological characteristics of the strain SD523 of the present invention were compared with other strains, consulting "Bergey's Manual of Systematic Bacteriology (1986)" and "Agriculture Handbook, No. 427, The Genus Bacillus (U.S. Dept. of Agr., 1973)".

From the facts that the strain SD523 is an aerobic bacillus which is gram-positive and has an ability of forming spores, it is clear that the strain SD523 belongs to the genus Bacillus. Since the strain SD523 is positive for catalase, negative for VP test, does not grow at 65° C., decomposes starch, produce no gas from glucose, does not assimilate citric acid, and so on, it is identified to be a bacterium belonging to *Bacillus firmus*.

However, the strain SD523 differs from *Bacillus firmus* in that SD523 grows at 50° C. but *Bacillus firmus* does not grow at that temperature.

On the other hand, various alkaline proteases produced by microorganisms belonging to the genus Bacillus and suitable for compounding with detergents are disclosed in, for example, Japanese Patent Application Laid-Open No. 13592/1973 (=U.S. Pat. No. 3,827,938), Japanese Patent Publication No. 8401/1976 (=U.S. Pat. No. 3,723,250) and No. 24512/1981 (=U.S. Pat. No. 4,002,572). Among the known strains, their bacteriological characteristics were compared with the strain SD523 in detail.

1) NRRL B1107 (Japanese Patent Application Laid-Open No. 13592/1973 (=U.S. Pat. No. 3,827,938)) is a strain belonging to *Bacillus firmus*, which grows at 50° C. like the strain SD523. Difference between them is that NRRL B1107 produces no acids from arabinose.

2) NCIB 10144, 10145 and 10319 (Japanese Patent Publication 8401/1976 (=U.S. Pat. No. 3,723,250)) also belong to *Bacillus firmus*, and grow at 50° C. These strains differ from SD523 in that they assimilate citric acid but the strain SD523 does not.

3) PB92 (FERM 3304) (Japanese Patent Publication No. 24512/1981 (=U.S. Pat. No. 4,002,572)) differ greatly from the strain SD523 in physiological properties and bacteriologically since PB92 produces no acids from many sugars such as glucose, fructose, sorbitol, mannitol, sucrose, and starch and has a different pH in VP broth.

As is clear from the aforementioned bacteriological properties, the strain SD523 of the present invention is identified to be a novel bacterial strain belonging to Bacillus firmus.

The strain Bacillus sp. SD523 was deposited at Fermentation Research Institute, Agency of Industrial Science and Technology, Ministry of International Trade and Industry, 1-3, Higashi 1 chome, Tgukuba-Shi, Ibaraki-Ken, 305, Japan under the terms of the "Budapest Treaty on the International Recognition of the Deposit of Microorganisms for the Purpose of Patent Procedure" under Accession No. Ferm BP-3774. The original deposit, designated FERM P-12113, was made on Mar. 30, 1991 and it was transferred to a deposit under the terms of the Budapest Treaty on Mar. 2, 1992.

Preparation of Enzyme

Protease produced by the strain Bacillus sp. SD523 was named "API-25". In order to obtain protease API-25 of the present invention using the strain SD523, it is sufficient to inoculate the strain SD523 in a suitable medium and cultivate it in a conventional manner.

The microorganism used in the present invention is not limited to the aforementioned strain SD523 (Ferm BP-3774) and any strain may be used so far as it has an ability of producing a protease having the properties described hereinbelow. The strain Bacillus sp. SD523 may include its spontaneous and artificial mutants, and genetically engineered variants.

Artificial mutants of Bacillus sp. SD523 can be obtained by a conventional method. For example, an original strain is subjected to artificial mutation treatment such as irradiation with ultraviolet rays or treatment with a chemical, e.g., N-methyl-N'-nitro-N-nitrosoguanidine (NTG) and then planted on an agar medium containing skimmed milk and cultivated to grow colonies. The colonies are isolated, and are then cultivated on a conventional medium for protease production, and the resulting protease is checked for identity. Thus, a strain having the most excellent productivity for the objective protease can be screened.

Also, genetically engineered strains can be obtained by a conventional method. For example, a presumption on DNA base sequence of the chromosome of the original strain is made based on amino acid sequence of protease produced by the original strain, and a characteristic portion of the presumed DNA base sequence is synthesized. Then, phosphorus atoms in the phosphoric acid groups in the sequence are labelled with radioisotope $^{32}P$. On the other hand, the entire chromosomal DNA is extracted from the original strain and digested with a suitable restriction enzyme to obtain DNA fragments, which are then subjected to Southern hybridization method to allow the chromosomal fragments to hybridize with the synthetic DNA. Thus, a chromosomal fragment which hybridizes with the synthetic DNA is screened.

The chromosomal fragment thus obtained is incorporated in a suitable vector and introduced in a protease non-producing strain and production of protease is checked. The DNA fragment of which protease production has been confirmed is introduced in the original strain or a strain having a higher enzyme productivity (i.e., having a higher ability of secreting proteins) using a suitable vector such as a plasmid to obtain a strain of which productivity has been improved.

Cultivation Method

Upon production of the protease of the present invention, there is no special requirement on the method for cultivating the aforementioned microorganism and it can be cultivated by a conventional method appropriately.

As the nutrient sources of the medium, any medium usually used for the cultivation of microorganisms may be used so far as the Bacillus strain of the present invention can grow thereon and produce alkaline protease. Carbon source may be any assimilable carbon compounds or those containing them, for example, glucose, maltose, sucrose, soluble starch, etc. Nitrogen source may be any assimilable nitrogen compounds or those containing them, for example, organic nitrogen source such as defatted soybean powder, defatted sesame powder, defatted bran, and corn steep liquor. In addition, inorganic salts such as phosphoric acid salts, potassium salts, and magnesium salts may be added.

In the present invention, cultivation may be carried out under aerobic conditions, for example, by aerated spinner culture or shaking culture. The cultivation temperature may be within the range of 20° to 40° C. but a range of 30° to 37° C. where best growth occurs is preferred. Initial pH may preferably be 9 to 10, and pH during cultivation may preferably be 8.5 to 10. The cultivation time may be within the range of about 16 to 60 hours, the cultivation may be stopped when the protease activity reaches a maximum value.

Isolation and Purification Methods

The protease of the present invention can be isolated and purified in a manner similar to conventional methods generally used for collecting enzymes. For example, cells and solid medium can be removed by centrifugation, filtration or the like to obtain a supernatant or filtrate.

From the solution thus separated, the protease of the present invention can be obtained by precipitation of proteins such as salting out method using soluble salts or solvent precipitation method using hydrophilic solvents, spray drying method, lyophilization method or the like. Further, the protease of the present invention can be purified by suitable conventional purification methods such as ion exchange chromatography and gel filtration chromatography in combination.

The properties of the alkaline protease of the present invention will be described in detail below.

Assay of Enzyme Activities

The activity of the alkaline protease of the present invention thus obtained can be measured by the following method.

(1) Hagiwara Variation

To 500 µl of a 50 mM Atkins-Pantin phosphate buffer solution (pH 10) is added 50 µl of an enzyme solution diluted appropriately, and the resulting mixture is preincubated at 30° C. for 3 to 5 minutes. Then, 500 µl of a 2% Hammerstein casein solution (pH 10) is added to the solution, and after 10 minutes 2 ml of TCA solution (0.132M TCA, adjusted to pH 4 with an acetate buffer solution) is added thereto to stop the reaction. After leaving it to stand at 30° C. for 10~15 minutes, the mixture is filtered using No. 2 filter paper (produced by Toyo Filter Paper Co., Ltd.). To 1 ml of the filtrate solution are added 5 ml of 0.4M sodium carbonate and 1 ml of 6-fold diluted phenol reagent. After leaving the mixture to stand at 30° C. for 20 minutes for color development, its optical density is measured at 660 nm.

Assay of the enzyme is expressed in terms of katal which is unity when the reaction is carried out at 30° C. at pH 10 using casein as a substrate, and proteinase activity for producing, in TCA-soluble fraction, a decomposate which develops color at 660 nm equivalent to 1 mole of tyrosine in 1 second is obtained.

2. TNBS Method

Amino acids produced by the action of protease dissolved in a borate buffer solution (pH 9.4) using 0.1% succinylcasein as a substrate are subjected to color development with 0.15 % trinitrobenzenesulfonic acid (TNBS) and the activity of the enzyme is measured by colorimetry. The measurement is performed at 50° C. automatically using TECHNICON Autoanalyzer (Trademark, Technicon Inc.).

The activity of the enzyme is expressed using a standard enzyme of which titer has been determined by the method 1 above as the internal standard.

Productivity of Protease API-25 and Specific Activity of Enzyme Produced

1. Comparison of Productivity

In order to supply stable enzyme at a low cost, microorganisms belonging to the genus Bacillus which generally exhibit high exogenous enzyme productivities are selected. Then, the productivity of the strain SD523 of the present invention is compared with the productivities of conventional protease-producing Bacillus strains (deposited strains).

Method: According to the cultivation method explained hereinbelow, the respective protease-producing strains are cultivated in a small jar fermentor (volume: 5 liter) under aerobic conditions, and their productivities are compared one with another.

Results: Results obtained are shown in Table 2. Comparison of activity is expressed in terms of relative activity assuming the productivity of the strain SD523 is 100.

It can be said that the productivity of the strain SD523 is at a high level despite the fact that it produces stable enzyme.

TABLE 2

| Strain | Productivity (Relative Value) | Duration of Maximum Activity (hr) |
|---|---|---|
| SD523 | 100 | 32–36 |
| NRRL B 1107 | 105 | 32–36 |
| NCIB 10144 | 60 | 32–36 |
| NCIB 10145 | 75 | 32–36 |
| NCIB 10319 | 50 | 32–36 |
| PB92 | 130 | 34–38 |

2. Comparison of Specific Activity

The specific activity of the enzyme API-25 produced by the strain SD523 is compared with that of the protease produced by the conventional Bacillus strains.

Method: The enzymes produced by the method 1 above are purified according to the purification method for API-25 described in the examples described hereinbelow, and the activities of the enzymes per unit protein are compared one with another. Determination of protein is carried out by microbiuret method and that of enzyme activity by the aforementioned Hagiwara variation.

Results: Results obtained are shown in Table 3. Comparison of specific activity is expressed in terms of relative activity assuming the specific activity of API-25 is 100.

It can be said that the specific activity of the enzyme API-25 is at a very high level as compared with other unstable enzymes despite the fact that it is a stable enzyme.

TABLE 3

| Enzyme | Specific Activity (Relative Value) |
|---|---|
| SD523 | 100 |
| NRRL B 1107 | 93 |
| NCIB 10144 | — |
| NCIB 10145 | 100 |
| NCIB 10319 | 92 |
| PB92 | 100 |

Properties of Enzyme API-25

1. Storage Stability in Liquid Detergents (1) Storage Stability in Model Liquid Detergent Model liquid detergent M-3 having the following composition is prepared.

| Composition (wt %) of Model Liquid Detergent M-3: | |
|---|---|
| LAS | 8 |
| AES | 12 |
| POEAE | 5 |
| PG | 5 |
| TEA | 1.5 |
| pH | 9.3 |

Notes: LAS: n-Dodecylbenzenesulfonate
AES: Alkylpolyoxyethylenesulfate
R—(CH$_2$CH$_2$O)$_3$SO$_3$Na (R = C$_{12}$ to C$_{15}$)
POEAE: Polyoxyethylene alkyl ether
RO—(CH$_2$CH$_2$O)$_n$H (R = C$_{12}$ to C$_{13}$, n = 5 to 7)
PG: Propylene glycol
TEA: Triethanolamine Method: Calcium (300 ppm) is added to a liquid detergent, and an enzyme is added thereto in an amount of 200 (nanokatal), and the mixture is stored at 40° C. Residual activity of the enzyme is measured by the aforementioned Hagiwara variation.

Results: As shown in Table 4 and FIG. 1, the enzyme API-25 is superior over the conventional enzymes in storage stability in the model liquid detergent which has a definite composition. Particularly, the enzyme API-25 is outstanding in the following two points: (1) its deactivation rate is lower than that of the other enzymes; and (2) half-life is at least about twice as long as that of the other enzymes.

TABLE 4

| Enzyme | Half-life (Days) | Residual Activity in storage (%) | | | | |
|---|---|---|---|---|---|---|
| | | 3 | 7 | 10 | 14 | 21 (Days) |
| API-25 | 17–18 | 82 | 75 | 66 | 56 | 45 |
| NRRL B 1107 | 6–8 | 65 | 52 | 35 | 22 | — |
| NCIB 10144 | 8–10 | 77 | 60 | 47 | 36 | — |
| NCIB 10145 | 8–10 | 77 | 60 | 49 | 37 | — |
| NCIB 10319 | 8–9 | 70 | 55 | 45 | 36 | — |
| PB92 | 8–10 | 83 | 65 | 46 | 40 | — |

(2) Storage Stability in Commercially Available Liquid Detergent

Method: Storage stability is tested in the same manner as in (1) above using a commercially available liquid detergent A-1 in place of the model liquid detergent M-3.

| Composition (wt %) of A-1 (Analytical results): | |
|---|---|
| LAS | 15 |
| POEAE | 5 |
| PG | 4 |
| Sodium citrate | 6 |
| Ethanolamine | 1.3 |
| Inorganic salts | 11 |
| pH | 9.4 |

Notes: The abbreviations of LAS, POEAE and PG denote the same meaning as in (1) above.

Figure 2:
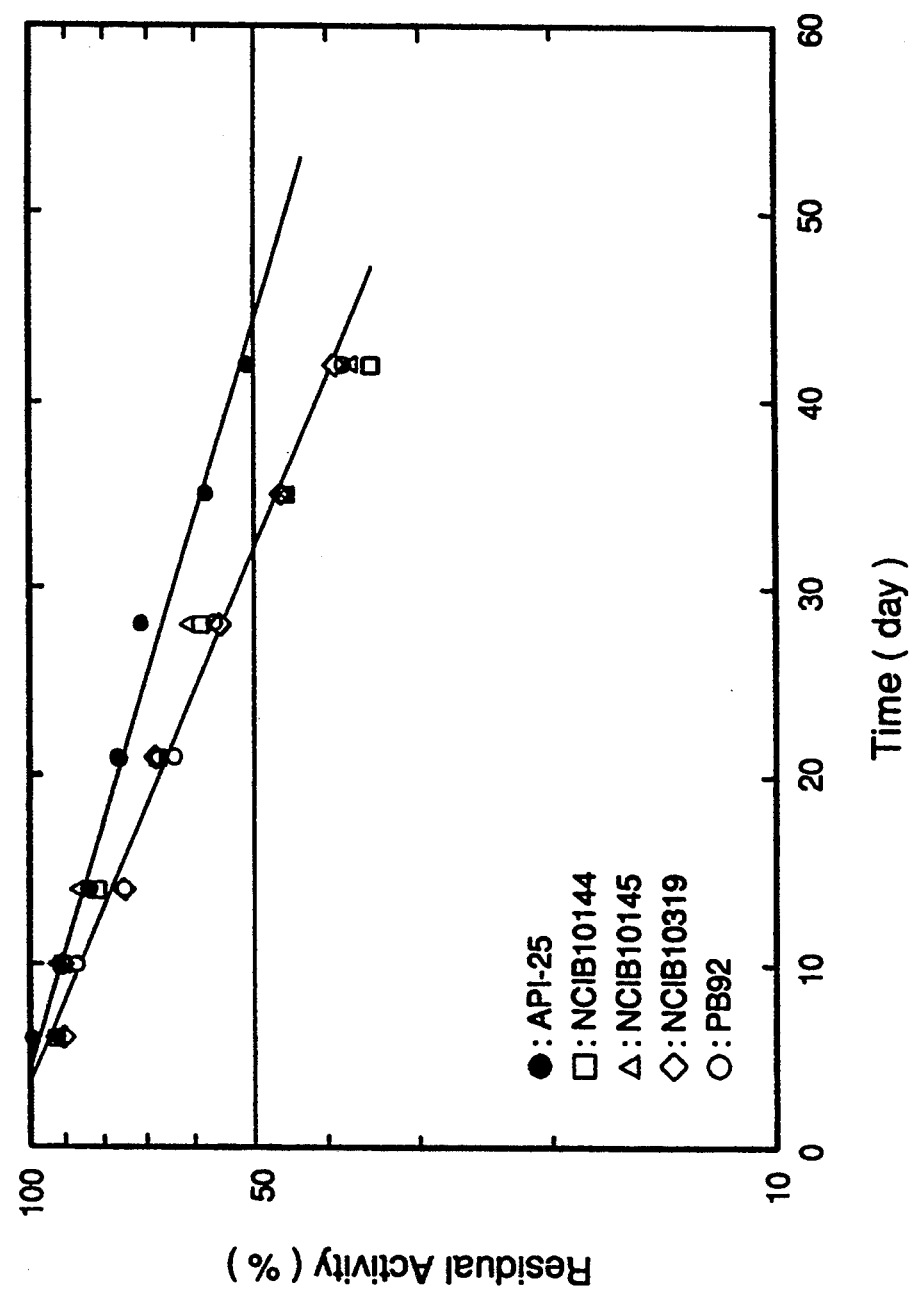
FIG. 2 is a graph illustrating storage stabilities of the enzyme of the present invention and conventional enzymes (4 types), respectively, in a commercially available liquid detergent A-1.

Results: As shown in Table 5 and FIG. 2, the enzyme API-25 is superior over the conventional enzymes in storage stability in the commercially available liquid detergent too. Particularly, the deactivation rate of the enzyme API-25 is lower than that of the other enzymes.

TABLE 5

| Enzyme | Half-life (Days) | Residual Activity in storage (%) | | | | | | |
|---|---|---|---|---|---|---|---|---|
| | | 6 | 10 | 14 | 21 | 28 | 35 | 42 (Days) |
| API-25 | 41–44 | 99 | 91 | 83 | 76 | 71 | 58 | 51 |
| NRRL B 1107 | — | — | — | — | — | — | — | — |
| NCIB 10144 | 31–33 | 92 | 90 | 81 | 67 | 59 | 45 | 35 |
| NCIB 10145 | 31–33 | 93 | 92 | 86 | 68 | 61 | 45 | 37 |
| NCIB 10319 | 31–33 | 91 | 90 | 75 | 68 | 56 | 46 | 39 |
| PB92 | 31–33 | 99 | 87 | 75 | 64 | 57 | 46 | 38 |

2. Stability in Surfactant (Detergent) Solutions (1) Stability in Solution of Anionic Surfactant, LAS Among the components of a detergent, that which gives the greatest influence on the deactivation of an enzyme compounded in the detergent is anionic surfactants. Accordingly, stabilities of the enzymes in LAS solutions which are known to give particularly strong damages to the enzymes are compared.

Method: Calcium (4 ppm) and LAS (2,000 ppm) are added to a 50 mM ATKINS-PANTIN borate buffer solution (pH 10), and an enzyme is added thereto in an amount of 200 nkatal/ml. The mixture is stored at 40° C. Residual activity of the enzyme is measured chronologically and expressed in terms of relative value assuming the initial activity of the enzyme just after the addition thereof is 100.

Figure 3:
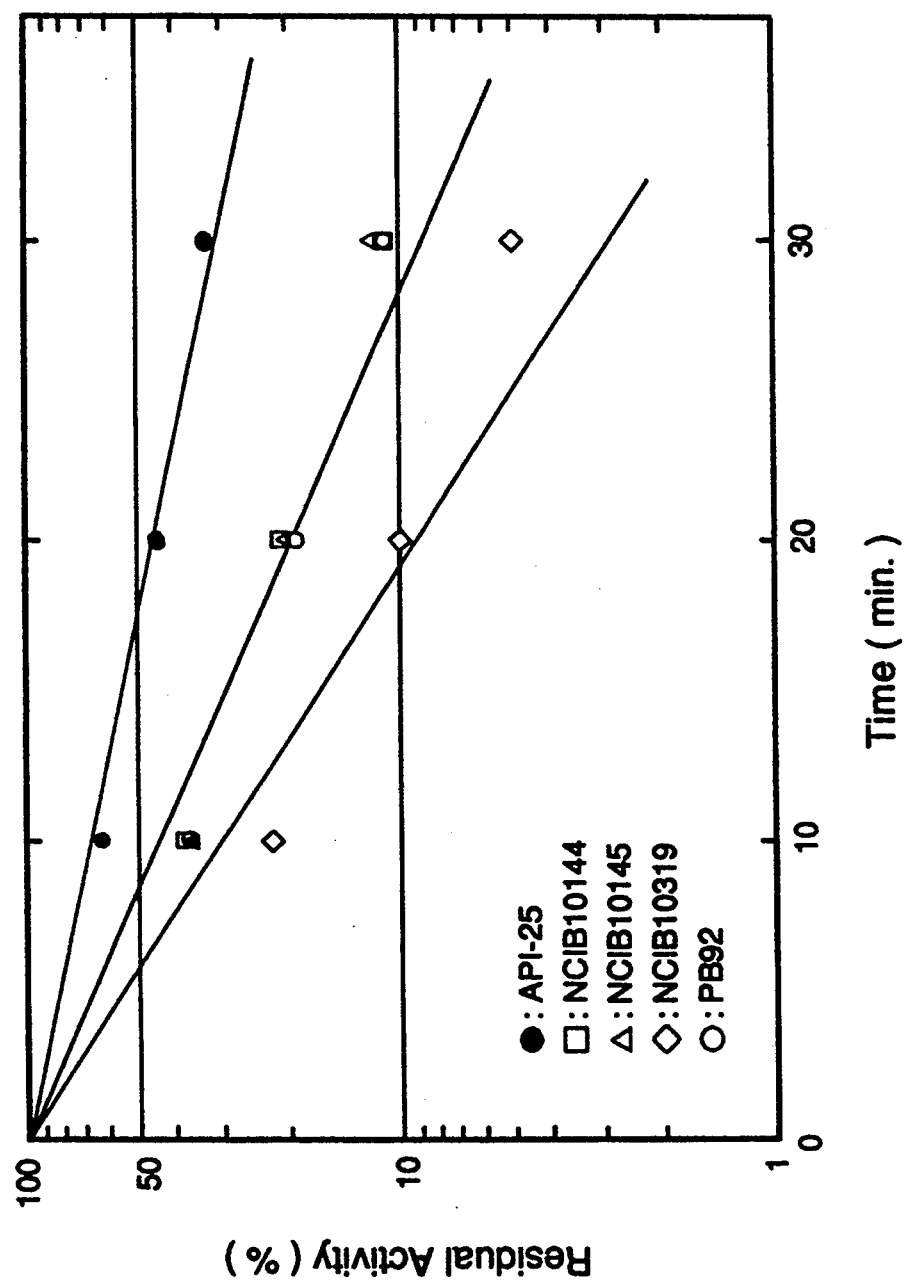
FIG. 3 is a graph illustrating stabilities of the enzyme of the present invention and conventional enzymes (4 types), respectively, in a LAS solution.

Results: As shown in Table 6 and FIG. 3, the enzyme API-25 is superior over the conventional enzymes in stability in the LAS solution. Particularly, the enzyme API-25 is outstanding in the following two points: (1) its deactivation rate is lower than that of the other enzymes; and (2) its half-life is by at least about twice as long as that of the other enzymes.

TABLE 6

| Enzyme | Half-life (min.) | Chronological Change of Residual Activity (%) | | |
|---|---|---|---|---|
| | | 10 | 20 | 30 (min.) |
| API-25 | 18–19 | 63 | 45 | 33 |
| NRRL B 1107 | — | — | — | — |
| NCIB 10144 | 7–9 | 38 | 21 | 11 |
| NCIB 10145 | 7–9 | 36 | 20 | 12 |
| NCIB 10319 | 4–6 | 22 | 10 | 5 |
| PB92 | 7–9 | 37 | 19 | 11 |

(2) Stability in Solutions of Commercially Available Liquid Detergent (A-I)

In order to compare the stabilities during actual washing, stabilities of enzymes in solutions of a commercially available detergent are compared.

Method: The commercially available detergent A-1 is used. Calcium (60 ppm) and the detergent A-1 (1.9 g/liter) are added to a 50 mM borate buffer solution (pH 9.4), and an enzyme is added thereto in an amount of about 100 nkatal/l. The mixture is stored at 50° C. Residual activity of the enzyme is measured chronologically by the TNBS method and expressed in terms of relative value assuming the initial activity of the enzyme just after the addition thereof to the solution of the detergent is 100.

Figure 4:
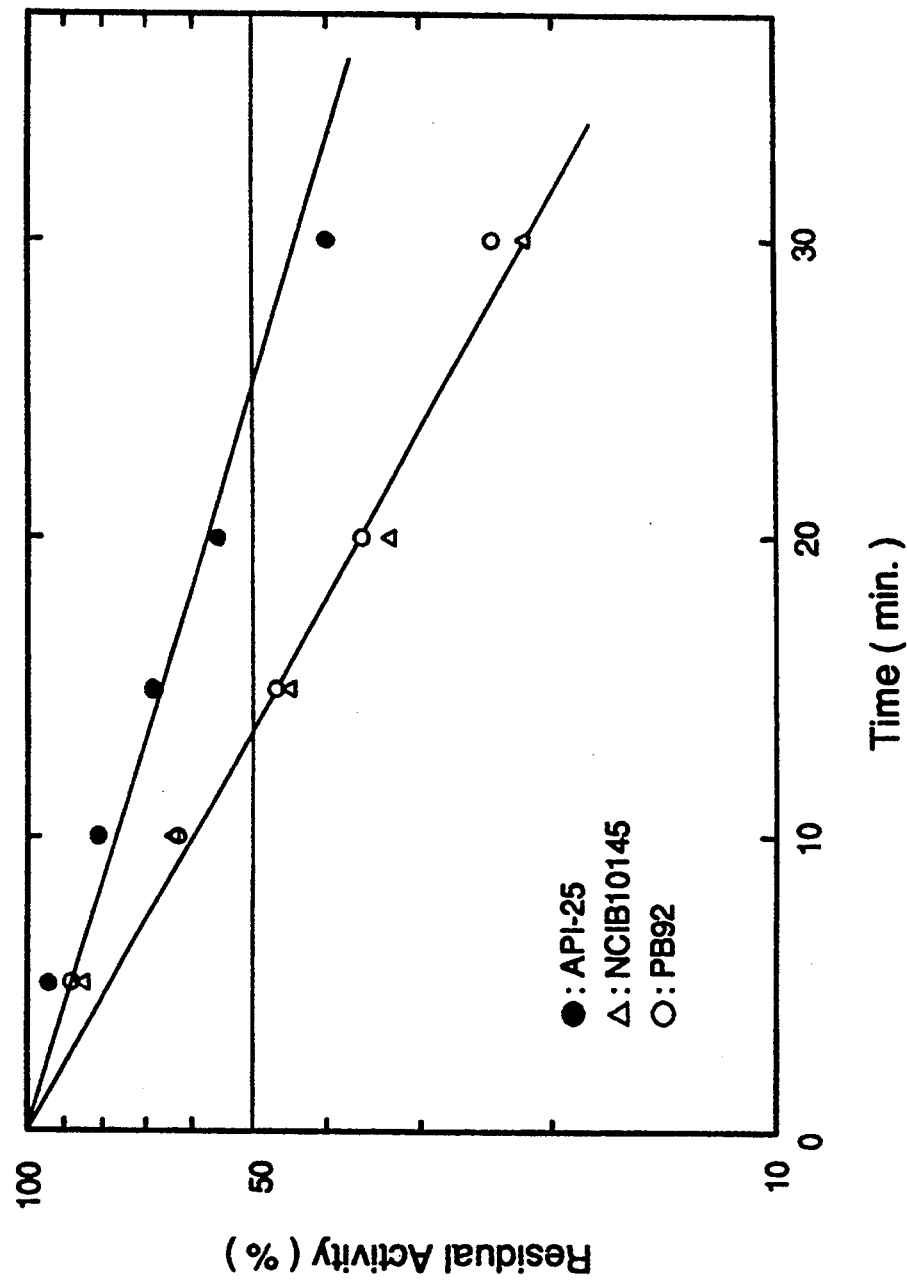
FIG. 4 is a graph illustrating stabilities of the enzyme of the present invention and conventional enzymes (2 types), respectively, in a diluted solution of a commercially available liquid detergent A-1.

Results: As shown in Table 7 and FIG. 4, the enzyme API-25 is superior over the conventional enzymes in stability in a model system simulating actual washing. Particularly, as in the case of the stability in LAS solution, the enzyme API-25 is outstanding in the following two points: (1) its deactivation rate is lower than that of the other enzymes; and (2) its half-life is by at least about twice as long as that of the other enzymes.

TABLE 7

| Enzyme | Half-life (min.) | Chronological change of Residual Activity (%) | | | | |
|---|---|---|---|---|---|---|
| | | 5 | 10 | 15 | 20 | 30 (min.) |
| API-25 | 23–27 | 94 | 81 | 68 | 56 | 40 |
| NRRL B 1107 | — | — | — | — | — | — |
| NCIB 10144 | — | — | — | — | — | — |
| NCIB 10145 | 12–15 | 85 | 64 | 45 | 33 | 22 |
| NCIB 10319 | — | — | — | — | — | — |
| PB92 | 12–15 | 88 | 63 | 47 | 36 | 24 |

3. Physical Chemical Properties of Enzyme (1) Action

The alkaline protease of the present invention hydrolyzes proteins such as casein, bovine serum albumin, ovalbumin, hemoglobin, and keratin.

(2) Substrate Specificity

The substrate specificity (% decomposition) of the alkaline protease of the present invention is as shown in Table 8 below.

TABLE 8

| Substrate | Decomposition rate[*] of Enzyme (%) | | | |
|---|---|---|---|---|
| | API-25 | NCIB10319 | NCIB10145 | PB92 |
| Ovalbumin | 67 | 53 | 54 | 55 |
| Bovine serum albumin | 43 | 56 | 57 | 55 |
| Hemoglobin | 97 | 97 | 97 | 92 |
| Keratin | 93 | 97 | 98 | 98 |

Note: [*]Decomposition rate of enzyme is expressed in terms of relative value assuming the activity obtained using undenatured casein as a substrate is 100%.

Conditions:

| Denaturation of substrate: | 100° C., pH about 10, 10 minutes; |
|---|---|
| Reaction: | pH 10, 30° C.; |
| Concentration of substrate: | 1% |
| Concentration of enzyme: | about 1 nkatal/ml |

(3) Optimum pH and Stable pH Range

Figure 5:
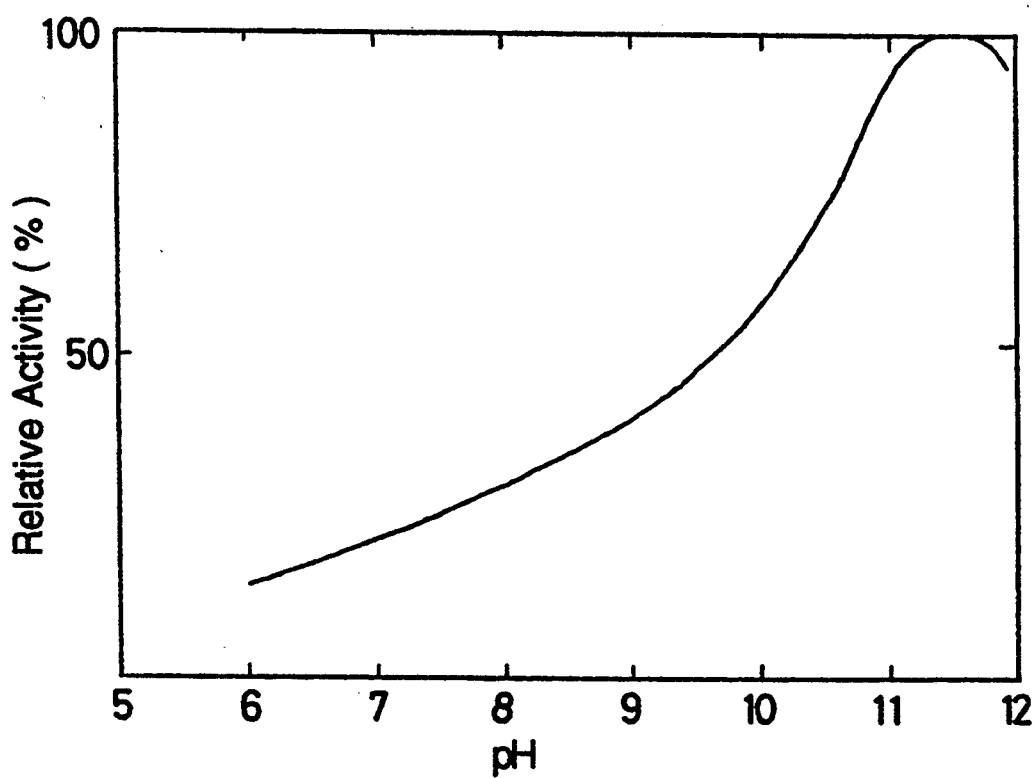
FIG. 5 is a graph illustrating an optimum pH range of the enzyme of the present invention.
Figure 6:
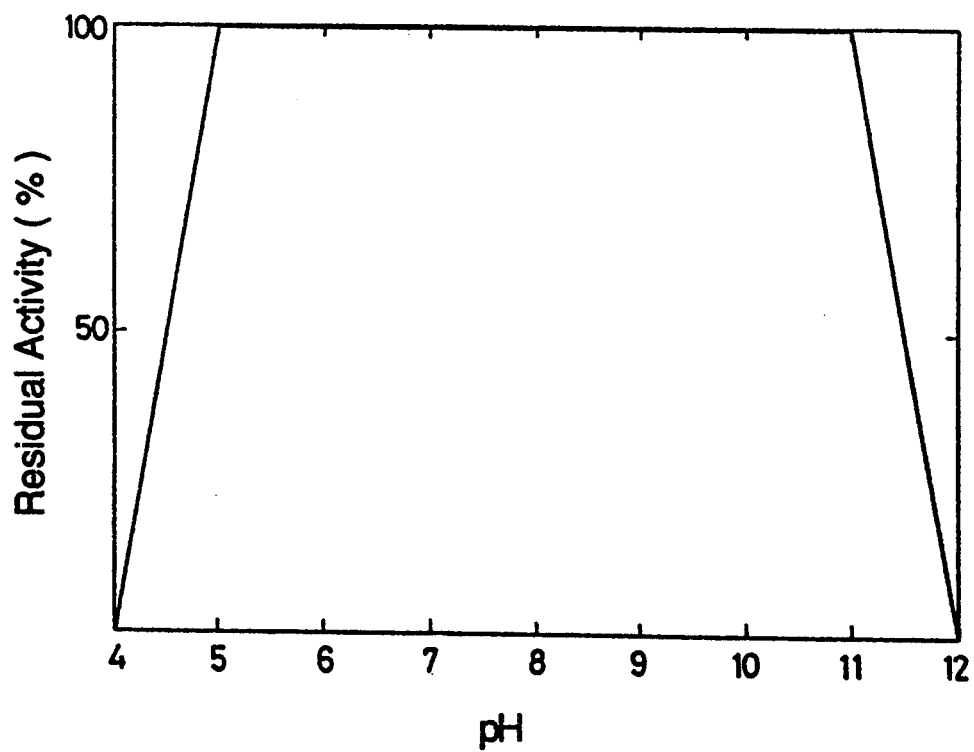
FIG. 6 is a graph illustrating a pH stability of the enzyme of the present invention.

The optimum pH and stable pH range of the alkaline protease of the present invention are measured, and results obtained are shown in FIGS. 5 and 6.

Method for measuring optimum pH: A wide range buffer solution of Britton-Robinson (pH 4 to 12) is used as a buffer solution. Upon measuring optimum pH, an enzyme solution in an amount of about 1 nkatal/ml is added to buffer solutions at different pH values containing 1% casein. After allowing the resulting mixtures to react at 30° C. for 10 minutes, the activities of the enzyme in the mixtures are measured.

Method for measuring stable pH range: The enzyme of the present invention is added to buffer solutions at different pH values so that the concentration of the enzyme is about 20 nkatal/ml. After incubating the resulting mixtures at 30° C. for 24 hours, the activities of the enzyme in the mixtures are measured. Residual activities are obtained at respective pH values assuming the activity of the enzyme before the incubation is 100%.

From FIG. 5, it can be seen that the enzyme of the present invention has an optimum pH within the range of about 11 to 11.5. Also, it can be seen from FIG. 6, the stable pH range of the enzyme of the present invention is 5 to 11 at 30° C.

(4) Optimum Temperature and Temperature Stability

Figure 7:
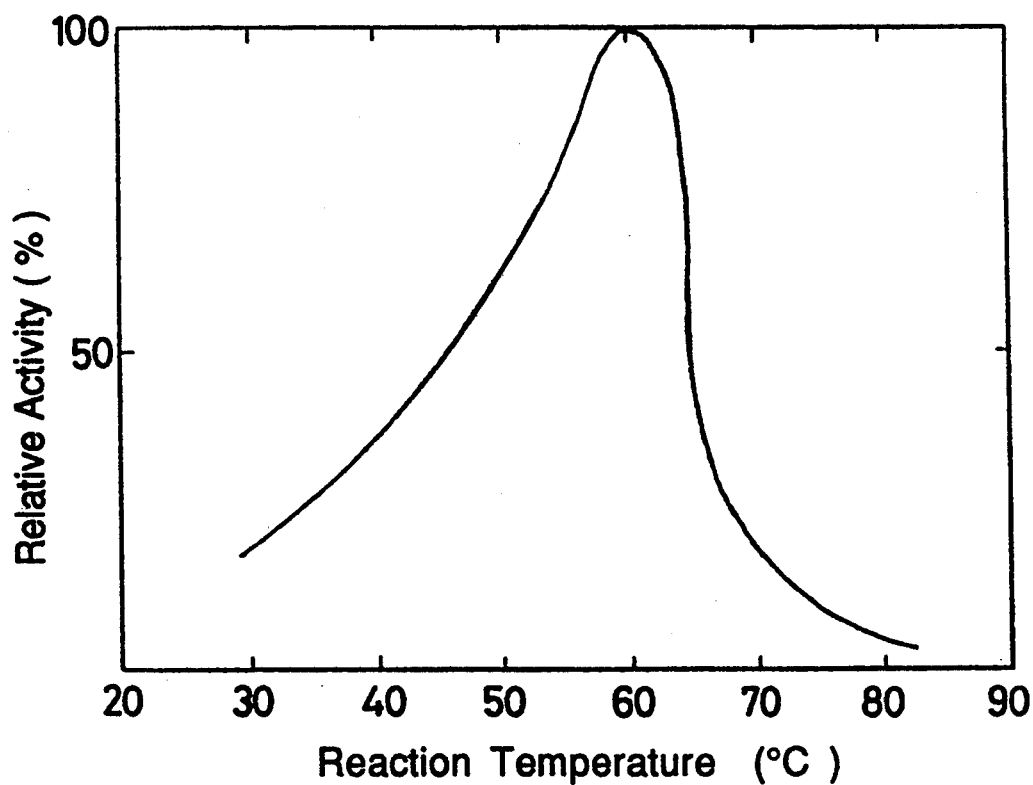
FIG. 7 is a graph illustrating an optimum temperature range of the enzyme of the present invention.
Figure 8:
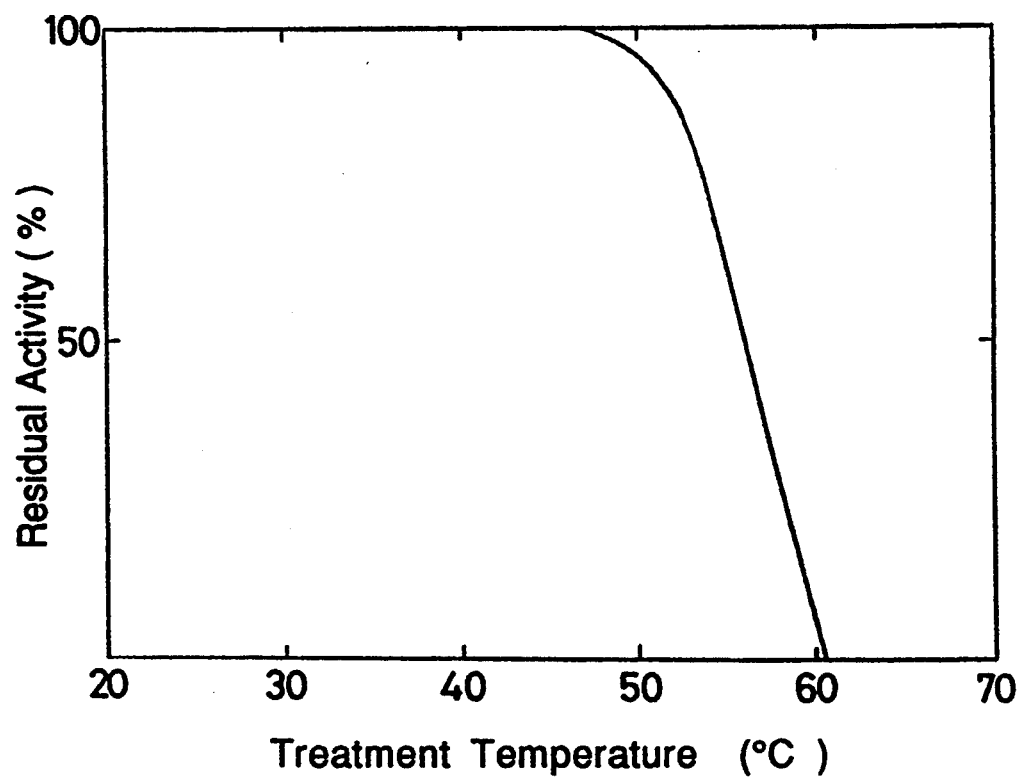
FIG. 8 is a graph illustrating a temperature stability of the enzyme of the present invention.

The optimum temperature and temperature stability of the enzyme of the present invention are shown in FIGS. 7 and 8.

Method for measuring optimum temperature: Aliquots of a 50 mM borate buffer solution (pH 10) containing 1% casein as a substrate are preincubated at various temperatures, respectively, for 5 minutes. Then, the enzyme of the present invention is added to each of the preincubated solutions. The resulting mixtures are allowed to react for 10 minutes at the respective temperatures. Relative activities at respective temperatures are obtained assuming the activity of the enzyme at 30° C. is 100.

Method for measuring temperature stability: The enzyme of the present invention is added to a 50 mM borate buffer solution (pH 10) so that the concentration of the enzyme is about 20 nkatal/ml. After incubating the resulting mixtures at various temperatures for 10 minutes, the mixtures are cooled, and the activities of the enzyme in the mixtures are measured.

From FIG. 7, it can be seen that the enzyme of the present invention has an optimum temperature at about 60° C. As will be understood from FIG. 8, the temperature at which the activity of the enzyme of the present invention is decreased to half the initial activity after heat treatment at pH 10 for 10 minutes is about from 55° to 57° C.

(5) Influence of Metal Ions

To a solution of the enzyme of the present invention prepared by diluting a stock solution in a 50 mM borate buffer solution (pH 10) so that the concentration of the enzyme is about 20 nkatal/ml are added various metal ions, respectively, so that the concentration of the metal ion is 1 mM. After incubating the resulting mixtures at 40° C. for 1 hour and 24 hours, the activity of the enzyme in the respective mixtures is measured in order to examine influence of the metal ions on the enzyme of the present invention. Results obtained are shown in Table 9, in which the activity is expressed in terms of relative activity assuming that the activity of the enzyme in the absence of metal salts just before the initiation of the treatment is 100%. As will be understood from Table 9, addition of copper sulfate and silver nitrate result in decrease in the activity of the enzyme of the present invention.

TABLE 9

Influence of Metal Ions

| Metal Salt | Relative Activity (%) Conditions of Treatment | |
|---|---|---|
| | 40° C., 1 hour | 40° C., 24 hours |
| None | 91 | 74 |
| $Na_2SO_4$ | 91 | 75 |
| $CuSO_4$ | 6 | 4 |
| $ZnSO_4$ | 92 | 72 |
| $FeSO_4$ | 87 | 74 |
| $CoCl_2$ | 92 | 65 |
| $MnCl_2$ | 93 | 71 |
| $AgNO_3$ | 81 | 29 |
| $BaCl_2$ | 90 | 72 |
| $MgSO_4$ | 95 | 79 |
| $CaCl_2$ | 93 | 90 |

(6) Stabilization Effect of Calcium Ion

Influence of calcium ion ($Ca^{2+}$) on the temperature stability of the enzyme of the present invention is examined under the conditions and by the method described below.

Enzyme solutions containing the enzyme of the present invention in a concentration of 20 nkatal/ml are prepared using a 50 mM borate buffer solution (pH 10) and the same borate buffer solution plus 1 mM calcium chloride, respectively. The enzyme solutions are subjected to heat treatment at 55° C. for 10 minutes. After ice-cooling, the residual activity of the enzyme solutions is measured. Results obtained are shown in Table 10, in which the activity is expressed in terms of relative activity assuming that the activity before the heat treatment is 100%.

TABLE 10

| | Residual Activity After Treatment (%) |
|---|---|
| None | 60 |
| $CaCl_2$ | 97 |

As will be understood from Table 10 above, the enzyme of the present invention exhibits a considerably increased stability in the presence of calcium ions.

(7) Influence of Enzyme Inhibitors

Influence of various inhibitors against the enzyme of the present invention is examined under the conditions and by the method described below.

Enzyme solutions containing the enzyme of the present invention in a concentration of 20 nkatal/ml are prepared using a 50 mM borate buffer solution (pH 10), respectively. Various inhibitors in concentrations as shown in Table 11 are added to the enzyme solutions, respectively. After incubating the resulting mixtures at 30° C. for 30 minutes, the residual activity of the enzyme in the mixtures is measured. Results obtained are shown in Table 11, in which the activity is expressed in terms of relative activity assuming that the activity in the absence of inhibitors is 100%.

TABLE 11

| Inhibitor | Concentration | Residual Activity (%) |
|---|---|---|
| None | — | 100 |
| PCMB | 1 mM | 98 |
| | 10 mM | 90 |
| PMSF | 1 mM | 31 |
| | 10 mM | 0.7 |
| EDTA | 10 mM | 104 |

Notes: PCMB: p-Chloromercuribenzoic acid
PMSF: Phenylmethanesulfonyl fluoride
EDTA: Ethylenediaminetetraacetic acid As will be clear from Table 11 above, the enzyme of the present invention is inhibited by phenylmethanesulfonyl fluoride (PMSF) considerably, which reveals that the enzyme is a serine protease.

(8) Molecular Weight:

Molecular weight of the enzyme of the present invention is measured by SDS polyacrylamide electrophoresis in Phast-System produced by Pharmacia using Phastgel G8-25 (Pharmacia). As a result, the molecular weight of the enzyme of the present invention is obtained by calculation to be 29,000±2,000.

EXAMPLES

Hereafter, the present invention will be explained in more detail by way of examples. However, the present invention is not limited thereto. Unless otherwise indicated specifically, all percentages and parts are by weight.

EXAMPLE 1

Two liters of a liquid culture medium composed of 2% defatted soybean powder, 2% maltose, 0.2% dipotassium hydrogenphosphate, 0.05% magnesium sulfate, and 1% sodium carbonate were introduced in a 5-liter culture tank, and sterilized with steam. SD523 strain cultivated in advance was inoculated in the culture tank. Then, aerated spinner culture was performed at 35° C. for 32 hours. Pellicles were removed from the culture broth to obtain a supernatant. The supernatant had a protease activity of about 600 nkatal/ml.

EXAMPLE 2: Purification of Enzyme API-25

Pellicles were removed from the culture broth obtained in Example 1 and the solution was concentrated using an ultrafiltration membrane. The concentrate obtained was subjected to salting out with 30 to 60 % saturation ammonium sulfate.

The precipitates thus obtained were dissolved in a 25 mM Tris-hydrochloric acid buffer solution (pH 7.5) containing 1 mM $CaCl_2$, and dialyzed against the same buffer solution.

Subsequently, the resulting solution was adsorbed on CM-cellulofine C-500 column (Seikagaku Kogyo Co., Ltd.) at pH 7.5 and eluted by a density gradient method using 0 to 1 M KCl containing 1 mM $CaC_2$ to recover an enzyme sample having a specific activity of about 6 times higher than that of the solution before the chromatography by CM-cellulofine C-500 column. The sample was subjected to SDS polyacrylamide gel electrophoresis to detect a single band. The purified enzyme thus obtained had the aforementioned substrate specificity, optimum pH, stable pH range, optimum temperature, temperature stability, influence of metal ions, stability in LAS solution, and molecular weight.

EXAMPLE 3: Washing Tests Using a Liquid Detergent Containing API-25

Washing effect of the enzyme of the present invention when added in the commercially available detergent A-1 was examined using a crude enzyme prepared by a conventional spray drying method.

To 1 liter of deionized water were added 60 ppm of calcium ion ($Ca^{2+}$), 2 g of liquid detergent A-1, and 100 nkatal of the crude enzyme, and a dirty cloth was washed with the resulting mixture. Whiteness of the cloth thus washed was measured. Comparison was made with the detergent composition containing no enzyme.

As the dirty cloth, 10 pieces of EMPA-116 (5×5 cm) were used. Results obtained are shown in Table 12.

TABLE 12

| | Efficiency of Washing |
|---|---|
| Enzyme added | 66 |
| No enzyme | 53 |

From the results shown in Table 12, it can be seen that the sample containing the enzyme of the present invention obviously has a washing power superior over the sample containing no enzyme, thus indicating that the enzyme of the present invention contributes to improvement of the washing power of liquid detergents.

What is claimed is:

1. An isolated alkaline protease from a microorganism belonging to the genus Bacillus and having the following properties:
   (1) an activity for hydrolyzing proteins;
   (2) an optimum pH of from about 11 to 11.5 as measured after reaction at 30° C. for 10 minutes using casein as a substrate;
   (3) an optimum temperature of about 60° C. as measured after reaction at pH 10 using casein as a substrate;
   (4) a heat resistance in terms of a half inactivation temperature of about from 55° to 57° C. as measured after incubation at pH 10 for 10 minutes;
   (5) a molecular weight of 29,000±2,000 as measured by using SDS polyacrylamide electrophoresis; and
   (6) a half-life of activity in a solution of 2000 ppm of the anionic surfactant, n-dodecylbenzenesulfonate, and 4 ppm calcium, pH 10, at 40° C. of longer than 10 minutes.

2. An aid for detergents, comprising the alkaline protease according to claim 1 as an effective ingredient and a surfactant.

3. The aid for detergents according to claim 2, wherein the surfactant is an anionic surfactant.

* * * * *

UNITED STATES PATENT AND TRADEMARK OFFICE
CERTIFICATE OF CORRECTION

PATENT NO.   : 5,387,518
DATED        : February 7, 1995
INVENTOR(S)  : Sawayanagi et al.

It is certified that error(s) appears in the above-identified patent and that said Letters Patent is hereby corrected as shown below:

Col. 5, line 8, delete "Tgukuba" and insert therefor --Tsukuba--.

Signed and Sealed this

Eighteenth Day of July, 1995

Attest:

BRUCE LEHMAN

Attesting Officer          Commissioner of Patents and Trademarks